United States Patent [19]
Merger et al.

[11] Patent Number: 5,247,120
[45] Date of Patent: Sep. 21, 1993

[54] PREPARATION OF AMINOPROPIONITRILES

[75] Inventors: Franz Merger, Frankenthal; Martin Brudermueller, Mannheim; Claus-Ulrich Priester, Ludwigshafen; Wolfgang Harder, Weinheim; Siegfried Winderl, Heidelberg, all of Fed. Rep. of Germany

[73] Assignee: BASF Aktiengesellchaft, Ludwigshafen, Fed. Rep. of Germany

[21] Appl. No.: 921,660

[22] Filed: Jul. 30, 1992

[30] Foreign Application Priority Data

Aug. 3, 1991 [DE] Fed. Rep. of Germany ....... 4125797
May 8, 1992 [DE] Fed. Rep. of Germany ....... 4215192

[51] Int. Cl.$^5$ ............................................ C07C 253/30
[52] U.S. Cl. ..................................................... 558/452
[58] Field of Search ......................................... 558/452

[56] References Cited

U.S. PATENT DOCUMENTS

| | | | |
|---|---|---|---|
| 2,019,903 | 11/1935 | Heitmann | 154/30 |
| 2,401,429 | 6/1946 | Kung | 260/464 |
| 2,432,511 | 12/1947 | Davis et al. | 260/464 |
| 2,448,013 | 8/1948 | Buc et al. | 260/465.5 |
| 2,742,491 | 4/1956 | Weijlard et al. | 260/465.5 |
| 3,174,992 | 3/1965 | McCracken | 260/465.5 |
| 3,914,280 | 10/1975 | Yamakami et al. | 260/465.5 R |
| 3,935,256 | 1/1976 | Verbeeck | 260/534 A |
| 4,743,702 | 5/1988 | Hoelderich et al. | 558/312 X |
| 4,967,006 | 10/1990 | Carr | 558/452 X |

FOREIGN PATENT DOCUMENTS

| | | |
|---|---|---|
| 1003740 | 7/1957 | Fed. Rep. of Germany . |
| 2436651 | 2/1975 | Fed. Rep. of Germany . |
| 457695 | 1/1975 | U.S.S.R. ............... 558/452 |
| 642403 | 9/1950 | United Kingdom . |

OTHER PUBLICATIONS

Bruson, "Organic Reactions", vol. 5, (1949), pp. 82-83 and 113.
The Chemistry of Acrylonitrile, 2nd Ed., (1959), Cyanamid, p. 155.
Chemical Abstracts, vol. 83, p. 879, Abs. No. 26879, Khakhlov et al. (1982).
Buc, S. R., B-Aminopropionitrile and bis-(B-Cyanoethyl)-Amine, Methods in Organic Synthesis, vol. 27, pp. 3-5 (1947).
Szlompek-Nesteruk, D., Prezemysl Chemiczny, vol. 44, (1965), pp. 86-87.
Goldberg, et al., Synthesis of W-Aminoalkyl Cyanides, J. Chem. Soc. No. 254, pp. 1369-1371 (1947).

Primary Examiner—Joseph Paul Brust
Attorney, Agent, or Firm—Keil & Weinkauf

[57] ABSTRACT

Abstract of the Disclosure: Aminopropionitriles of the general formula I

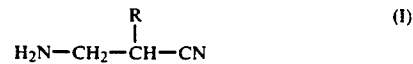

where R is hydrogen or methyl, wherein ammonia is reacted with an acrylonitrile of the general formula II

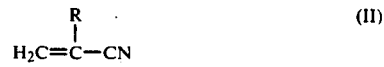

where the substituents have the abovementioned meanings, in a molar ratio of from 1:1 to 500:1 over a heterogeneous catalyst at from 40° to 180° C. and from 10 to 350 bar.

10 Claims, No Drawings

PREPARATION OF AMINOPROPIONITRILES

The present invention relates to a novel and improved process for the preparation of aminopropionitriles by reacting excess ammonia with an acrylonitrile over a heterogeneous catalyst at elevated temperature and pressure.

J. Chem. Soc. (1947), 1369-1371 describes the reaction of ω-bromoalkyl cyanides with a potassium salt of phthalimide and subsequent reaction with hydrazine hydrate. However, this process is unsuitable, for example, for the industrial production of 3-aminopropionitrile.

US-A 3,174,992 discloses the reaction of ethylenecyanohydrin with ammonia over moist Raney nickel at about 100° C. under autogenous pressure. The reaction takes place with a yield of 54% and is therefore unsatisfactory.

3-Aminopropionitrile and bis(2-cyanoethyl)amine are also obtained in an unfavorable ratio of 2:1 by the circuitous route via 2-methoxypropionitrile by reaction with ammonia in the presence of Raney cobalt at 65° to 80° C. and at 165 bar according to DE-A-10 03 740.

For the preparation of 3-aminopropionitrile by direct reaction of acrylonitrile with ammonia, it is known that anhydrous ammonia does not react at room temperature with acrylonitrile but instead can be used as a stabilizer for acrylonitrile (U.S. Pat. No. 2,432,511). U.S. Pat. No. 2,401,429 discloses that 76% of bis(2-cyanoethyl) ether well as 11% of 3-aminopropionitrile can be isolated from acrylonitrile and liquid ammonia at room temperature after 2 days. At 90° C. and under superatmospheric pressure, acrylonitrile is converted as liquid ammonia into 12.5% of 3-aminopropionitrile (DE-A-598 185).

It is also known that the addition of protic solvents has an advantageous effect on the addition reaction of NH3 with acrylonitrile. The addition of steam to the mixture of acrylonitrile and ammonia is disclosed in, for example, Chem. Abstr. Vol. 83, 26879. Usually, however, aqueous ammonia is used in the temperature range from 80° to 130° C. With a ratio of ammonia to acrylonitrile to water of 5-15:1:5-20, 3-aminopropionitrile is obtained, in addition to bis(2-cyanoethyl)amine, in yields of from 57 to 80% (eg. U.S. Pat. No. 3,935,256—62%, DE-A-24 36 651—70%, U.S. Pat. No. 2,448,013—78%, U.S. Pat. No. 2,819,903—59%, Org. Syn. (1947), 27, 3 to 5 - 57%). The disadvantages of these processes using aqueous ammonia arise in the working up or further processing of the product mixture:

Removal of added water by distillation in the recycle procedure required owing to large amounts of ammonia Lower selectivity for 3-aminopropionitrile in the separation of ammonia/water Hydrolysis of the nitrile groups Damage to the catalyst in the subsequent hydrogenation.

Przemyst Chem. 44(2) (1965), 85 and GB-A-642 409 disclose processes in which a yield of 81% of 3-aminopropionitrile is obtained by adding from 15 to 20 equivalents of methanol. The formation of byproducts by methylation prevents the industrial use of the process. On the other hand, a yield of 68% of 3-aminopropionitrile is obtained when 3 equivalents of tert-butanol are added (US-A 2,742,491).

The preparation, described in DE-A-24 36 651, of 3-aminopropionitrile by aminolysis of bis(2-cyanoethyl)amine with ammonia requires temperatures of from 130° to 170° C. and takes place very slowly with reaction times of up to 165 minutes.

It is an object of the present invention to remedy the abovementioned disadvantages.

We have found that this object is achieved by a novel and improved process for the preparation of aminopropionitrile of the formula I

where R is hydrogen or methyl, wherein ammonia is reacted with an acrylonitrile of the formula II

where the substituents have the abovementioned meanings, in a molar ratio of from 1:1 to 500:1 over a heterogeneous catalyst at from 40° to 180° C. and from 10 to 350 bar.

The novel process can be carried out as follows: The reaction can be effected at from 40° to 180° C. and from 10 to 350 bar, batchwise or preferably continuously. The preferred continuous process can be carried out at from 40° to 150° C. and from 10 to 200 bar, preferably from 50° to 120° C. and from 150 to 230 bar.

Ammonia containing from 0 to 5% by weight of water, preferably essentially anhydrous ammonia (from 0 to 1% by weight of water), particularly preferably ammonia containing from 0.1 to 1% by weight of water, is usually used with the acrylonitriles in a molar ratio of from 1:1 to 500:1, preferably from 2:1 to 100:1, particularly preferably from 10:1 to 80:1. Ammonia not converted in the reaction can be recycled to the reaction in a technically simple manner without adversely affecting the yield of aminopropionitrile.

In general, no solvents are used; however, inert solvents, for example ethers, such as dibutyl ether, tetrahydrofuran or dimethyl ether, or, for example, hydrocarbons, such as cyclohexane, benzene or toluene, may be employed in amounts of from 0 to 500, preferably from 50 to 200% by weight for the acrylonitrile II.

In the reaction, a space velocity of from 0.1 to 10, preferably from 0.1 to 2, g of acrylonitrile per g of catalyst per hour is advantageously maintained.

Particularly suitable heterogeneous catalysts are acidic and/or basic or amphoteric oxides of elements of the second, third or fourth main group, in particular various modifications of $Al_2O_3$ and $SiO_2$ in the form of silica gel, kieselguhr, quartz or mixtures of these, and of the second to sixth subgroups of the Periodic Table or mixtures of these. Further advantageous catalysts are zinc, oxide titanium oxide, zirconium oxide, vanadium oxides, niobium oxide, boron oxide, chromium oxides, molybdenum oxides, tungsten oxides or mixtures of these. Mixtures of these oxides with alumina are also suitable for this reaction. Further catalysts for the novel process are zeolites, phosphates or heteropoly acids.

Other suitable heterogeneous catalysts are lanthanum oxide and/or oxides of the lanthanides, such as cerium oxide, praseodymium oxide, and neodymium oxide, preferably cerium oxide, or mixtures thereof with acid and/or basic or amphoteric oxides of elements of the second, third and fourth main groups of the Periodic Table, in particular various modifications of $Al_2O_3$ and $SiO_2$ in the form of silica gel, kieselguhr or mixtures of these.

The aminopropionitriles of the formula I which are used in this process are: 3-aminopropionitrile and 3-aminoisobutyronitrile.

The aminopropionitriles of the formula I which can be prepared by the novel process are intermediates for the preparation of diamines, aminocarboxylic acids or aminocarboxamides.

The 3-aminopropionitrile of the formula I which can be prepared by the novel process is suitable as an intermediate for the preparation of

| | |
|---|---|
| β-amino acids: β-alanine → | Intermediate for calcium pantothenate by hydrolysis (DE-A 22 23 236) |
| 1,3-propylenediamine, | which is used in drugs, polyamides and wood preservatives (DE-A 32 48 326, DE-C 2004405) |

EXAMPLES

Example 1

A mixture of 270 ml of liquid ammonia and 20 ml of acrylonitrile (space velocity 0.8 g of acrylonitrile per g of catalyst per hour) was pumped, at 90° C. and 180 bar, through a tubular reactor filled with 19.8 g of $SiO_2$ (from 1 to 3 mm chips). The conversion was 99%. After an operating time of 100 hours, the reactor exit mixture had the following composition (quantitative GC): 85.1% by weight of 3-aminopropionitrile 13.0% by weight of bis(2-cyanoethyl)amine 0.9% by weight of acrylonitrile

Example 2

A mixture of 280 ml of liquid ammonia and 21 ml of acrylonitrile (space velocity 0.8 g of acrylonitrile per g of catalyst per hour) is pumped, at 130° C. and 180 bar, through a tubular reactor filled with 20.7 g of boron zeolite ZBM-11 ($SiO_2/B_2O_3 = 33.9$, 2.5 mm extrudates). After operation for 4 hours, conversion of 94% was obtained and a reactor exit mixture had the following composition (quantitative GC):
84.7% by weight of 3-aminopropionitrile
14.3% by weight of bis(2-cyanoethyl)amine
3.0% by weight of acrylonitrile

Example 3

275 ml of liquid ammonia and 20 ml of acrylonitrile (space velocity 0.57 g of acrylonitrile per g of catalyst per hour) were pumped, at 110° C. and 180 bar, over 28 g of zeolite ZSM-11 ($SiO_2/Al_2O_3 = 145.7$, 2.5 mm extrudates) arranged in a tubular reactor. After operation for 4 hours, a reactor exit mixture having the following composition (quantitative GC) was isolated (conversion 97%): 80.0% by weight of 3-aminopropionitrile 14.9% by weight of bis(2-cyanoethyl)amine 3.1% by weight of acrylonitrile

Example 4

280 ml of liquid ammonia and 20 ml of acrylonitrile were passed over 33 g of an 8:2 mixture of alumina and silica (from 2 to 3 mm grit) in a tubular reactor (space velocity: 0.48 g of acrylonitrile per g of catalyst per hour). At 90° C. and 180 bar, the reactor exit mixture had the following composition (quantitative GC) after an operating time of 48 hours at a conversion of 100%:
90.6% by weight of 3-aminopropionitrile
9.4% by weight of bis(2-cyanoethyl)amine

Example 5

290 ml of liquid ammonia and 20 ml of acrylonitrile (space velocity 0.48 g of acrylonitrile per g of catalyst per hour) were pumped, at 55° C. and 180 bar, over 33 g of alumina (from 1 to 33 mm grit) which had been introduced into a tubular reactor. After 400 hours of operation, a conversion of 97% was achieved and a reactor exit mixture having the following composition (quantitative GC) was isolated:
77.6% by weight of 3-aminopropionitrile
20.2% by weight of bis(2-cyanoethyl)amine
2.2% by weight of acrylonitrile

Example 6

A mixture of 275 ml/h of liquid ammonia and 20.7 ml/h of acrylonitrile (space velocity 0.13 g of acrylonitrile per g of catalyst per hour) was pumped, at 90° C. and 200 bar, through a tubular reactor filled with 125 g of cerium oxide (from 1 to 2 mm chips). The conversion was 92%. After an operating time of 50 hours, the reactor exit mixture had the following composition (quantitative GC):
59.1% by weight of 3-aminopropionitrile
30.6% by weight of bis(2-cyanoethyl)amine
10.3% by weight of acrylonitrile

Example 7

A mixture of 276.6 ml/h of liquid ammonia and 21.5 ml/h of acrylonitrile (space velocity 0.49 g of acrylonitrile per g of catalyst per hour) was pumped, at 50° C. and 200 bar, through a tubular reactor filled with 35.5 g of the catalyst alumina/cerium oxide (70% by weight/30% by weight; from 1 to 2 mm chips). The conversion was >99%. After an operating time of 70 hours, the reactor exit mixture had the following composition (quantitative GC):
77.0% by weight of 3-aminopropionitrile
22.4% by weight of bis(2-cyanoethyl)amine
0.7% by weight of acrylonitrile

Example 8

A mixture of 273.3 ml/h of liquid ammonia and 16.5 ml/h of acrylonitrile (space velocity 0.38 g of acrylonitrile per g of catalyst per hour) was pumped through a tubular reactor filled with 35.5 g of catalyst alumina/cerium oxide (70% by weight/30% by weight; from 1 to 2 mm chips). The conversion was >99%. After an operating time of 30 hours, the reactor exit mixture had the following composition (quantitative GC):
85.4% by weight of 3-aminopropionitrile
14.0% by weight of bis(2-cyanoethyl)amine
0.6% by weight of acrylonitrile

We claim:

1. A process for the preparation of an aminopropionitrile of the formula I

where R is hydrogen or methyl, which comprises: reacting ammonia with an acrylonitrile of the formula II

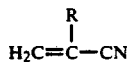

where the substituents have the abovementioned meanings, in a molar ratio of from 1:1 to 500:1 over a heterogeneous catalyst at from 40° to 180° C. and from 10 to 350 bar, said heterogeneous catalyst being an oxide of the second or third or fourth main group or of the second to sixth subgroup of the Period Table of elements, an acidic zeolite or a mixture thereof.

2. A process for the preparation of an aminopropionitrile as claimed in Claim 1, wherein R is hydrogen.

3. A process for the preparation of an aminopropionitrile as claimed in claim 1, wherein the heterogeneous catalyst used is an acidic heterogeneous catalyst.

4. A process for the preparation of an aminopropionitrile as claimed in claim 1, wherein ammonia is used with an acrylonitrile II in a molar ratio of 10:1 to 80:1.

5. A process for the preparation of an aminopropionitrile as claimed in claim 1, wherein the reaction is carried out at from 50° to 120° C.

6. A process for the preparation of an aminopropionitrile as claimed in claim 1, wherein the reaction is carried out at from 150 to 230 bar.

7. A process as defined in claim 1, wherein the heterogeneous catalyst is alumina.

8. A process as defined in claim 1, wherein the heterogeneous catalyst is silica.

9. A process as defined in claim 1, wherein the heterogeneous catalyst is a mixture of silica and alumina.

10. A process as defined in claim 1, wherein the heterogeneous catalyst is a mixture of silica and $B_2O_3$.

* * * * *